US00RE38817E

(19) United States
(12) Reissued Patent
Slettnes

(10) Patent Number: US RE38,817 E
(45) Date of Reissued Patent: Oct. 11, 2005

(54) METHOD AND SYSTEM FOR VELOCITY-NORMALIZED POSITION-BASED SCANNING

(75) Inventor: Tor Slettnes, Castro Valley, CA (US)

(73) Assignee: Applera Corporation, Foster City, CA (US)

(21) Appl. No.: 10/073,899

(22) Filed: Feb. 14, 2002

Related U.S. Patent Documents

Reissue of:
(64) Patent No.: 6,040,586
Issued: Mar. 21, 2000
Appl. No.: 09/073,130
Filed: May 5, 1998

(51) Int. Cl.[7] ..... G01N 15/06
(52) U.S. Cl. ..... 250/573; 204/612
(58) Field of Search ..... 250/573, 208.1, 250/234; 204/612; 382/129, 133

(56) References Cited

U.S. PATENT DOCUMENTS

| | | | | |
|---|---|---|---|---|
| 3,952,584 A | * | 4/1976 | Lichstein | 73/73 |
| 4,520,504 A | * | 5/1985 | Walker et al. | 382/100 |
| 4,620,200 A | | 10/1986 | Fukai | 347/235 |
| 5,072,382 A | * | 12/1991 | Kamentsky | 382/133 |
| 5,192,412 A | * | 3/1993 | Kambara et al. | 204/612 |
| 5,483,075 A | | 1/1996 | Smith et al. | 250/458.1 |

FOREIGN PATENT DOCUMENTS

| | | |
|---|---|---|
| JP | 61-89765 | 5/1986 |
| JP | 1-194743 | 8/1998 |
| WO | WO 96/13716 | 5/1996 |

OTHER PUBLICATIONS

West et al., 377 XE Software Package Overview, website—http://serac.mbt.washington.edu/Software/377XE/STC_Software_377XE_Index.html, pp. 1–7 (Last Edited on Jul. 29, 1997).*

Tibbetts, Clark, "Raw Data File Formats, and the Digital and Analog Raw Data Streams of the ABI Prism 377 DNA Sequencer," website—tibbetts@ctrvax.vanderbilt.edu, pp. 1–35 (Aug. 1995).*

English–language translation of Japanese Office Action issued in Japanese Patent Application No. 2000–547462.

* cited by examiner

*Primary Examiner*—Thanh X. Luu
(74) *Attorney, Agent, or Firm*—Finnegan, Henderson, Farabow, Garrett & Dunner, L.L.P.

(57) ABSTRACT

A data collection method for scanning a scan window comprising one or more channels is described. In the method of the invention an integrated signal (S) is measured across a scan window including one or more channels using an integrating detector. Next, a velocity-normalized integrated signal (Sn) is determined based on the integrated signal (S) and a scan velocity.

65 Claims, 10 Drawing Sheets

METHOD AND SYSTEM FOR VELOCITY-NORMALIZED POSITION-BASED SCANNING

Matter enclosed in heavy brackets [ ] appears in the original patent but forms no part of this reissue specification; matter printed in italics indicates the additions made by reissue.

FIELD OF THE INVENTION

This invention relates to methods, software and apparatus useful for scanning one or more channels using an integrating detector. More specifically, this invention relates to means for scanning which compensates for variable scanning velocities.

BACKGROUND

Scanning refers to a process whereby an integrated signal is obtained from one or more channels using an integrating detector which serially interrogates each channel. Such scanning systems are used in a variety of applications including text scanners, bar-code scanners, and electrophoresis scanners. A particularly important class of scanning systems are utilized in automated fluorescence-based DNA sequencing systems, e.g., U.S. Pat. Nos. 4,811,218; 5,091,652, 5,274,240, 5,102,785 and 5,543,026.

There are two important classes of scanning systems: position-based scanners and time-based scanners. In time-based scanners, a fixed integration time is used to collect an integrated signal from one or more channels of an object to be scanned. A feature of time-based scanning systems is that they provide low levels of time-dependent background signal. However, time-based scanners have the drawback that they generally display poor position repeatability, largely because of non-uniform scanning velocities due to acceleration/deceleration of the scanner and/or imperfect scanner repeatability. That is, the location of scan channels can vary from scan to scan. For example, in the case of an electrophoresis scanner, poor position repeatability may lead to poor lane tracking performance, i.e., it becomes impossible to distinguish a lane from neighboring lanes. This problem can become particularly severe when the density of lanes becomes high.

In position-based scanners, the integration time is based on a width of a channel and a scan velocity. Thus, rather than integrating a signal over a specified time, the signal is integrated over a specified distance, i.e., a channel width. Position-based scanners generally have superior positional repeatability. Thus, in the electrophoresis scanning application, position-based scanners exhibit superior lane tracking performance. However, position-based scanners display a high level of background noise because of non-uniform integration times resulting from the non-uniform scanning velocities mentioned above. Because signal strength is proportional to integration time, such non-uniform integration times result in high levels of time-dependent background noise.

Thus, it would be desirable to produce a scanner which combines the superior position repeatability of a position-based scanner with the low noise level of a time-based scanner.

SUMMARY

The present invention is directed towards the discovery of scanning systems which normalize an integrated signal intensity with respect to a scan velocity in order to achieve superior scanning performance.

It is an object of the present invention to provide a scanning system which provides superior positional repeatability.

It is another object of the present invention to provide a scanning system which has a reduced sensitivity to non-uniform scanning velocity.

In a first aspect, the foregoing and other objects of the invention are achieved by a method for scanning a scan window comprising one or more channels comprising the steps of first detecting an integrated signal (S) across a scan window comprising one or more channels using an integrating detector, then calculating a velocity-normalized integrated signal (Sn).

In another aspect, the present invention comprises a program storage device readable by a machine, tangibly embodying a program of instructions executable by a machine to perform the above method steps.

In yet another aspect, the present invention includes An apparatus for scanning a plurality of channels comprising means for detecting an integrated signal (S) across a scan window comprising one or more channels using an integrating detector, and computer means for calculating a velocity-normalized integrated signal (Sn).

These and other objects, features, and advantages of the present invention will become better understood with reference to the following description, drawings, and appended claims.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

The invention is based in part on the discovery that by normalizing an integrated signal with respect to a scan velocity in a position-based scanning system, scanning performance can be substantially improved. In particular, the magnitude of a time-dependent background noise level is substantially reduced.

I. DEFINITIONS

Unless stated otherwise, the following terms and phrases as used herein are intended to have the following meanings:

"Channel" means a region over which an integrating detector collects an integrated signal. In particular, a channel comprises a start point, an end point and a read region. E.g., where an integrating detector is a CCD, the pixels or bins of the CCD are charged across a channel.

A "scan window" as an array of neighboring channels which are serially interrogated, e.g., a collection of channels representing multiple lanes of a multi-lane electrophoresis system.

"Integrated signal" means a signal which is accumulated over an integration time and where a signal strength is a function of the integration time. For example, in the case of a CCD detector, the integrated signal is that amount of charge built up over an integration time as a result of an exposure to light.

"Integrating detector" means a detector which collects an integrated signal. Exemplary integrating detectors include but are not limited to charged coupled devices, photodiode arrays, charge injection devices, and active pixel CMOS detectors.

"Velocity-normalized integrated signal" means an integrated signal which has been normalized with respect to a scan velocity. For example, in one preferred method of velocity normalization, an integrated signal S is divided by a scan velocity v to give a velocity-normalized integrated signal, Sn.

II. SCANNING METHOD

Figure 1:
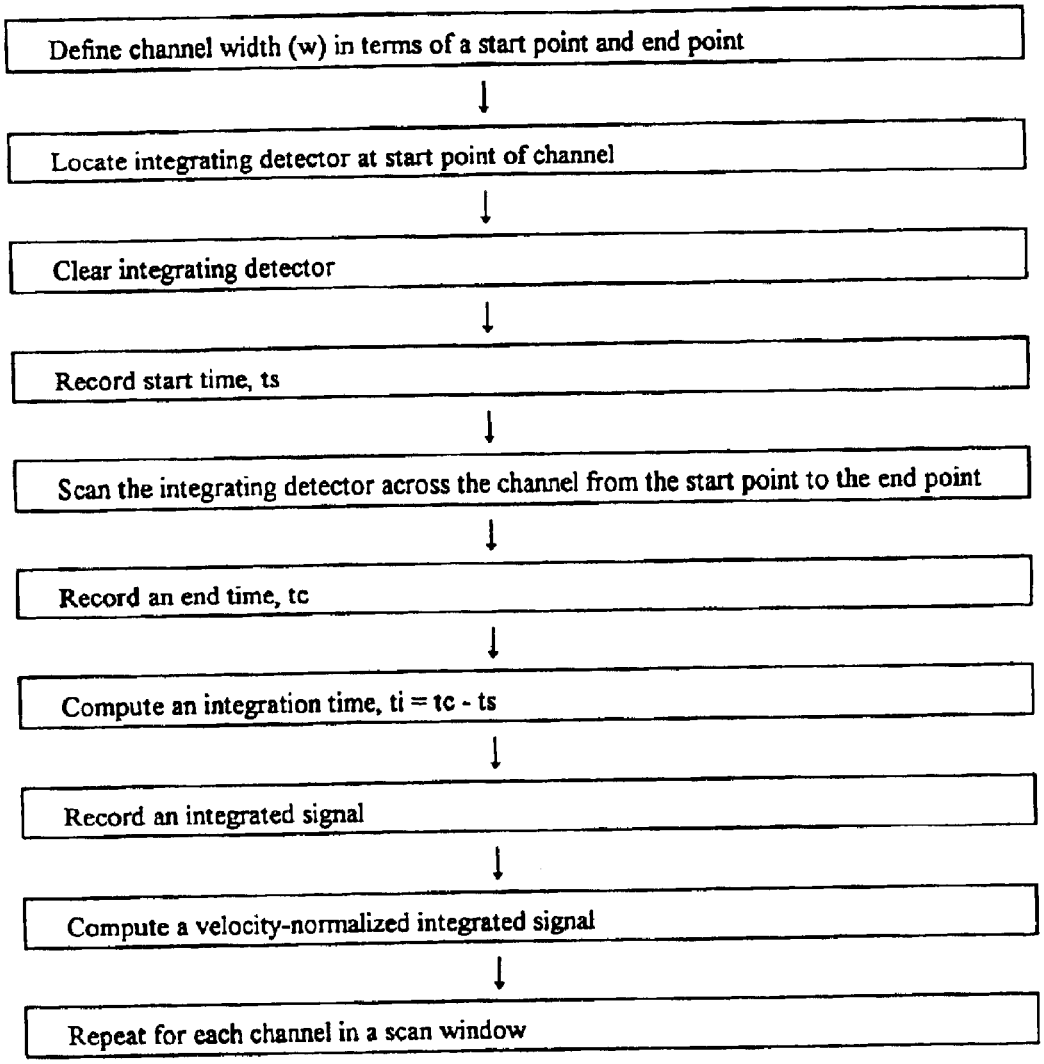
FIG. 1 is a process flow diagram illustrating the steps of the scanning method of the invention.

Generally, the scanning method of the invention is set forth in the process flow diagram of FIG. 1.

First, a channel is defined in terms of a start point, an end point and a channel width, w. Where multiple channels are to be scanned, each channel will be individually defined. In the case of an electrophoresis scanner, a given electrophoresis lane should preferably comprise at least three scan channels. For example, an electrophoresis system using a slab gel electrophoresis format and having 96 electrophoresis lanes is scanned using a scan window 17.5 cm across and subdivided into 480 channels.

Next, the integrating detector is positioned at the start point of the first channel to be scanned. Preferably, the detector is positioned relative to the channels using a stepper motor, and the precise relative location of the detector is determined by monitoring the encoder counts of the stepper motor and having an initial home position determined by a position sensor.

Prior to scanning the first channel, the integrating detector is cleared, i.e., any residual integrated signal residing in the detector is purged from the detector. In the case of a CCD detector, the detector is cleared by discharging all of the active registers. Also, prior to beginning the scan, a start time, ts, is recorded.

Next, the integrating detector is scanned across the channel from the start point to the end point by effecting a relative motion between the detector and the channel. This relative motion can be effected by moving the detector, moving the channel, moving an excitation light beam, e.g., using a galvo mirror, or any combination of such movements. Preferably, the end point is determined by counting the steps of a stepper motor used to effect the relative motion between the detector and the scan channels. When the scan has reached the end point of the channel, an end time, te, is recorded and an unnormalized integrated signal, S, is recorded. Following the scan, an integration time is calculated by computing the difference ts−te.

Figure 2:
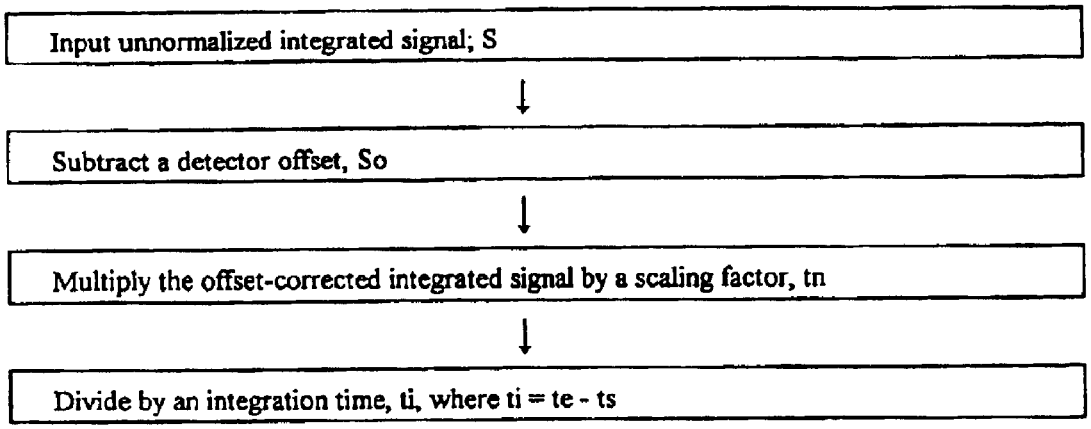
FIG. 2 is a process flow diagram illustrating the steps of the velocity-normalization aspect of the scanning method of the present invention.

The unnormalized integrated signal S is then normalized with respect to scan velocity by dividing the unnormalized integrated signal by a scan velocity, v. FIG. 2 shows a process flow diagram of a preferred method for performing the velocity normalization.

First, a detector offset, So, is subtracted from the unnormalized signal to give an offset-adjusted unnormalized signal. The detector offset is a time-independent background signal characteristic of the particular integration detector employed. It is desirable to remove the detector offset component of the integrated signal so as to avoid dividing a time-independent quantity by a time dependent quantity. In a preferred method for determining So, a channel is scanned using a first integration time, t1, and a first integrated signal, S1, is recorded. Then, the channel is rescanned using a second integration time, t2, and a second integrated signal, S2, is recorded. Finally, a linear extrapolation of signal vs. integration time is performed and the value of So is the zero-integration-time intercept of the extrapolation.

Next, the offset-adjusted unnormalized signal is multiplied by a scaling factor, tn, in order to expand the scale of the normalized signal. This scale expansion is performed to provide enhanced dynamic range and granularity to the velocity -normalized signal, Sn. Preferably, the value of tn is a nominal, or expected, integration time.

Finally, the offset adjusted, scaled signal is divided by the integration time, ti, resulting in a velocity normalized integrated signal, Sn.

Thus, the above operations can be summarized in the following equation relating unnormalized and normalized integrated signals, $$Sn = \frac{(S - So)tn}{ti}.$$

For scan windows comprising multiple channels, the above described normalization method is performed on each channel individually. For example, in a 96-lane electrophoresis system, 480 channels are used to scan the 96 lanes, each channel being normalized according to the method of the invention. In addition, the scan window may be repeatedly scanned to obtain additional information.

IV. SCANNER

The scanner of the present invention may be any apparatus which allows for the acquisition of an integrated signal across a scan window comprising one or more channels. Preferably, the scanner of the present invention is adapted to scan multiple electrophoresis lanes in a multi-lane electrophoresis system using laser-induced fluorescence detection, e.g., U.S. Pat. Nos. 4,811,218; 5,091,652, 5274240, and 5,543,026.

Generally, such electrophoresis scanners comprise (1) an integrating detector for collecting an integrated signal across an electrophoresis lane or portion thereof, (2) a light source for producing a light beam to excite fluorescence emissions from samples located in the electrophoresis lanes, (3) a scanning mechanism for the sequential interrogation of each of the one or more lanes seriatim, and (4) a computer for controlling the above elements and performing data acquisition and data normalization functions. Optionally, the scanner may include an electrophoresis system comprising one or more electrophoresis lanes for electrophoresing one or more samples simultaneously, e.g., for performing real-time measurements.

Figure 9:
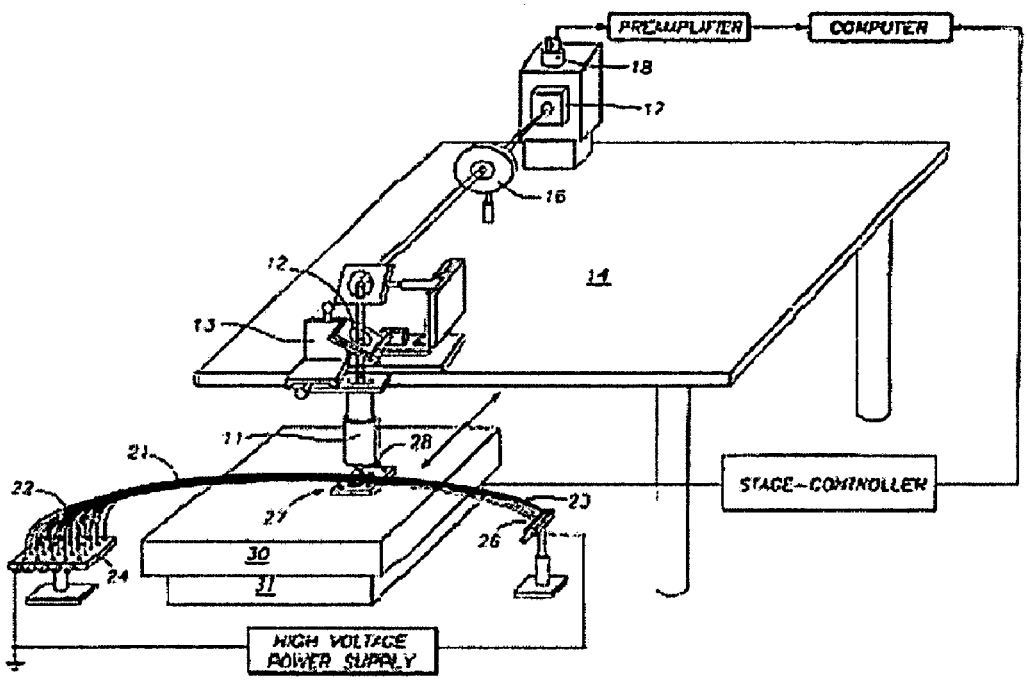
PRIOR ART FIG. 9
*FIG. 9 is a schematic diagram of a confocal-fluorescence capillary array scanner in accordance with one embodiment of the invention.*
Figure 10:
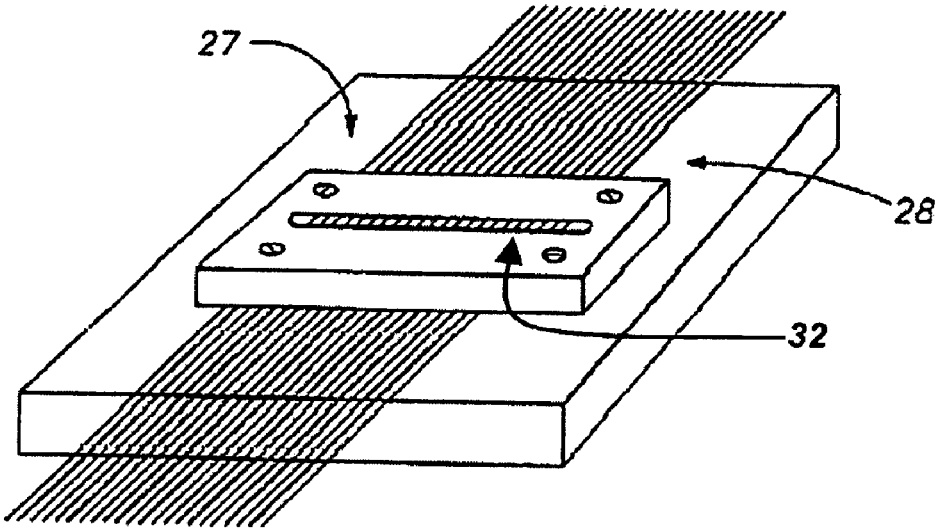
PRIOR ART FIG. 10
*FIG. 10 is a view of a holder for supporting a region of the capillaries in a side-by-side relationship.*

*An exemplary confocal fluorescence detection system for use with capillary arrays is shown in FIG. 9. An argon ion laser (Model 2020, Spectra-Physics, Mountain View, Calif.), not shown, is used as the excitation source. The laser beam is expanded to 5 mm diameter, collimated, and then directed through a 32 X, N.A. 0.4 infinite conjugate objective 11 (LD Plan-Achromat 440850, Carl Zeiss, West Germany) by a long-pass dichroic beamsplitter 12 (480 DM, Omega Optical, Brattleboro, Vt.). The dichroic beam splitter 12 reflects the excitation laser beam into the objective 11 but transmits fluorescent light collected by the objective which is Stokes shifted to longer wavelengths. The objective focuses the exciting laser on the sample and gathers the fluorescence with very high collection efficiency. The use of an infinite conjugate objective permits vertical adjustment of the probe volume by translating the objective with the mount 13 secured to the base 14 with no significant perturbation of the optical alignment. The focused 1 mW, 488 nm wavelength beam is focused to a 10 μm beam diameter and a 25 μm confocal beam parameter. The fluorescence emission is passed back through the long-pass dichroic beam splitter 12 mounted on the base 14 to reduce laser interference and to separate the excitation and detection paths. The fluorescence is then focused by a 75 mm focal length lens 16 mounted on the base 14 onto a 400 μm pinhole which serves as the confocal spatial filter. The light passing through the pinhole is filtered by a 488 nm rejection band filter (488 RB filter, Omega Optical, Brattleboro, Vt.), a long-pass cutoff filter (Schott GG-495, Esco, Oakridge, N.J.), a bandpass fluorescence filter (530 DF60, Omega Optical, Brattleboro, Vt.), all mounted within the housing 17, followed by detection with a cooled photomultiplier tube 18 (RCA 31034A, Burle Industries, Lancaster, Pa.). The spatial filter, the optical filters and photomultiplier tube are mounted on base 14. The output of the phototube is amplified and filtered with a low-noise amplifier (SR560, Standford Research Systems, Sunnyvale, Calif.), digitized with a 12 bit analog-to-digital board (DASH-16 F, metra-Byte, Taunton, Mass.) and stored in an IBM PS/2 microcomputer. The capillary array comprises a plurality of capillaries 21 having their ends 22, 23 extending into wells 24, 26 between which a high voltage is applied for electrophoresis. The ends 22 may be separated for individual manipulation and loading. A portion 27 of the capillaries is maintained in side-by-side parallel coplanar relationship by a holder 28, FIG. 10. The holder 28 includes a window 32 through which the beam can be focused on the interior volume of the capillaries. The holder 28 is mounted on a translation stage 30 (Model 4000, Design Components, Franklin, Mass.), which is actuated by stepper motor 31 (see FIG. 9).*

The integrating detector of the electrophoresis scanner may be any detector capable of collecting an integrated fluorescence signal. Preferred integrating detectors include charged coupled device detectors and photodiode array detectors.

The light source used in the electrophoresis scanner is preferably a laser, e.g., an argon ion, a helium-neon laser or a solid-state laser. The laser light may be directed parallel to the plane of the electrophoresis lanes of otherwise.

The scanning mechanism of the electrophoresis scanner may be any mechanism which provides for serial interrogation of each of the one or more electrophoresis lanes. In one alternative configuration, the light beam and the integrating detector are both translated across the electrophoresis lanes, e.g., by providing relative motion between the light beam and detector and the electrophoresis lanes. Such relative motion may be achieved by moving the light beam and detector, the electrophoresis lanes, or both the light beam and detector and the electrophoresis lanes. The scanner may scan the electrophoresis lanes during electrophoresis, i.e., real-time detection, or after the electrophoretic separation has been completed, i.e., off-line detection.

The electrophoresis system may be of conventional construction including one or more electrophoresis lanes, a voltage source, electrodes, buffer reservoirs, and the like. The electrophoresis lanes may be formed in a conventional slab gel, be independent channels formed in a continuous substrate, e.g., channels etched in a glass or plastic substrate, be located in discrete capillary tubes, or be in a flow-cell located at the outlet end of one or more capillary tubes, e.g., U.S. Pat. No. 5,439,578. Preferably, in the present invention, the electrophoresis lanes are formed in a slab gel, and more preferably the lane density is at least 1.8 mm/lane.

The computer of the scanner may be any conventional digital or analog computer. See Section V below.

V. COMPUTER SYSTEM AND PROGRAM STORAGE DEVICE

The steps of above-describe scanning method are preferably performed by a computer. In one preferred embodiment, the computer is made up of a processing unit, memory, I/O device, and associated address/data bus structures for communicating information therebetween. The microprocessor can take the form of a generic microprocessor driven by appropriate software, including RISC and CISC processors, a dedicated microprocessor using embedded firmware, or a customized digital signal processing circuit (DSP) which is dedicated to the specific processing tasks of the method. The memory may be within the microprocessor, i.e., level 1 cache, fast S-RAM, i.e., level 2 cache, D-RAM, or disk, either optical or magnetic. The I/O device may be any device capable of transmitting information between the computer and the user, e.g., a keyboard, mouse, network card, and the like. The address/data bus may be PCI bus, NU bus, ISA, or any other like bus structure.

When the method is performed by a computer, the above-described method steps are embodied in a program storage device readable by a machine, such program storage device including a computer readable medium. Computer readable media include magnetic diskettes, magnetic tapes, optical disks, Read Only Memory, Direct Access Storage Devices, gate arrays, electrostatic memory, and any other like medium.

VI. EXAMPLE

The invention will be further clarified by a consideration of the following examples, which are intended to be purely exemplary of the invention and not to in any way limit its scope.

EXAMPLE 1

Comparison of Noise Levels With and Without Velocity Normalization Using a Fixed Fluorescence Target Time-dependent noise levels were measured on an ABI PRISM™ 377 DNA Sequencer having a 96-lane capacity using scan windows having either 480 or 388 channels. Noise was measured using a dummy target fixture attached to the collection optics of the 377 system. The target was designed to mimic the actual background levels seen in DNA sequencing experiments. The target consisted of an outer housing containing two pieces of glass, each 1cm in diameter and having the same thickness as a standard sequencing plate, i.e., approximately 5 mm. The two glass discs were placed flat on top of one another and held in place by the outer housing. When screwed to the detector the housing held the two glass pieces in front of the laser beam. The glass served to provide a small reproducible fluorescent background and to scatter a portion of the laser light into the detector, thereby simulating actual running conditions. The scattered laser light and fluorescence were measured by the detection system of the 377.

The 377 instrument was turned on several hours before starting the experiment to ensure that the laser and electronics were equilibrated to the normal operating temperature.

The fixed target was used to collect data across a 480-channel scan window with firmware versions 2.2.j and 2.2.n. Data were also collected using 388-channel scan window with firmware versions 2.0, 2.2j and 2.2.n. Each data set was collected for ten minutes using the fixed target and the Plate Check A run module software. Other instrument settings were as follows: CCD gain=2; CCD offset=0; CCD pixel position 212; laser power 40.0 mW; no temperature control= room temperature and pump off; electrophoresis voltage off; Virtual Filter 1: pixel 161–185=530–540 nm; Virtual Filter 2: pixel 214–236=554–564 nm Virtual Filter 3: pixel 273–295=581–592 nm Virtual Filter 4: pixel 336–358=610–621 nm. Data were written to the standard ABIF gel image file format. Data were imported and analyzed using a Lab View data analysis package. One hundred and four scans were collected in each 10 minute run. Twenty five scans were discarded at the beginning of each run. The final scan of each run was also discarded. This left 78 scans for analysis. The average and standard deviation of signal intensity of each channel over the 78 scans were calculated. The signal-to-noise ratio was calculated for each channel by dividing the average signal by the standard deviation of the signal.

Figure 3:
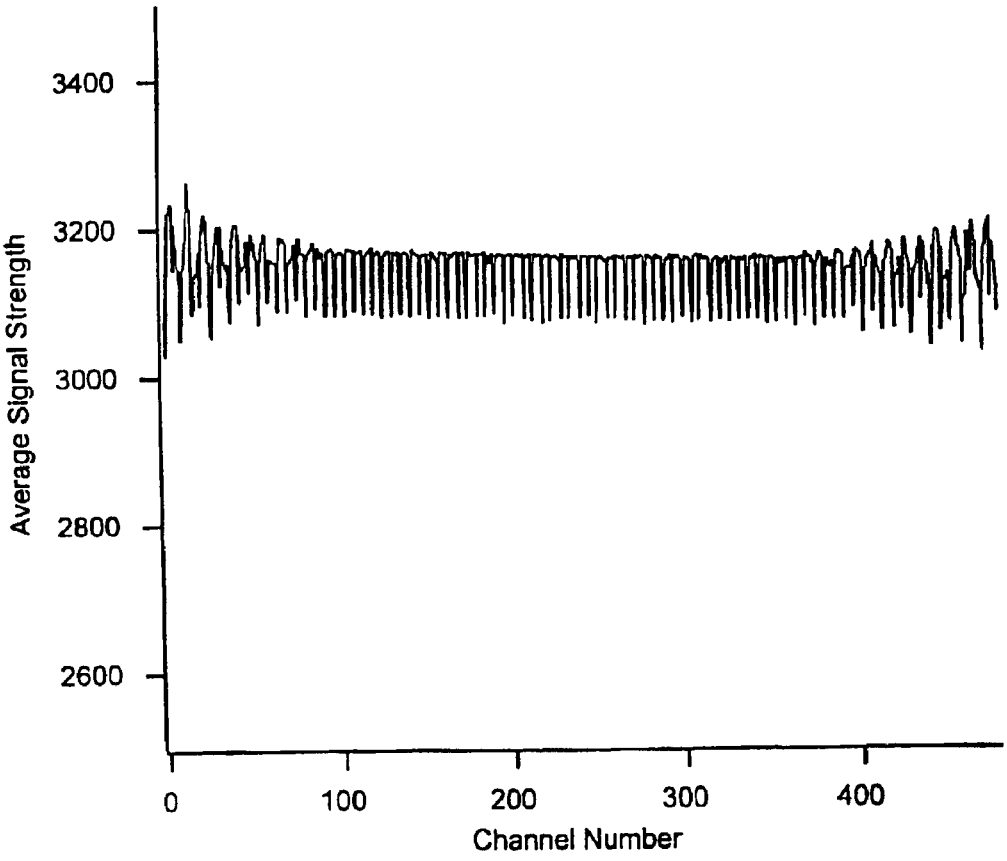
FIG. 3 is a plot of average signal strength versus channel position for 78 scans of a 480-channel scan window using position-based data collection without velocity normalization.
Figure 4:
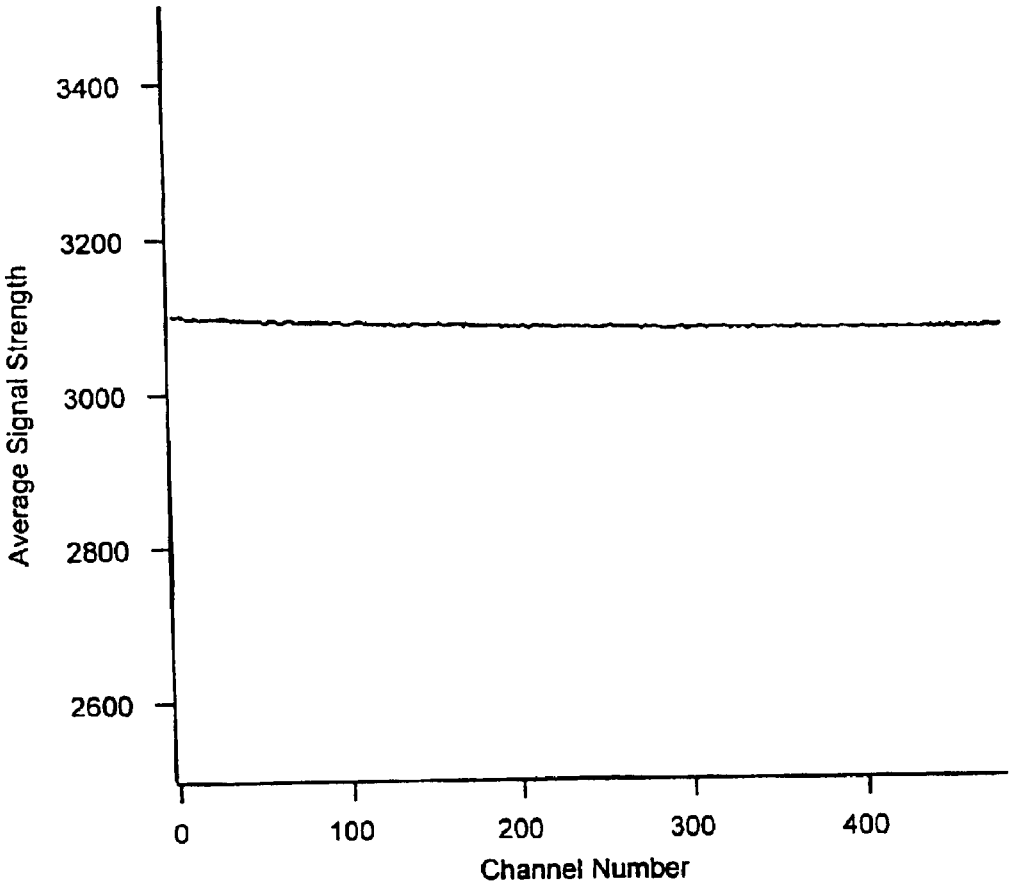
FIG. 4 is a plot similar to FIG. 3 but showing collected employing the velocity-normalized position based collection method of the present invention.

FIG. 3 is a plot of the average signal strength versus channel position for 78 scans of a 480-channel scan window collected with position-based collection without velocity normalization. FIG. 4 is a plot of similar data collected using the velocity-normalized position based collection method of the present invention. As can be seen from the Figures, the signal is less noisy when the velocity normalization scanning method is utilized.

Figure 5:
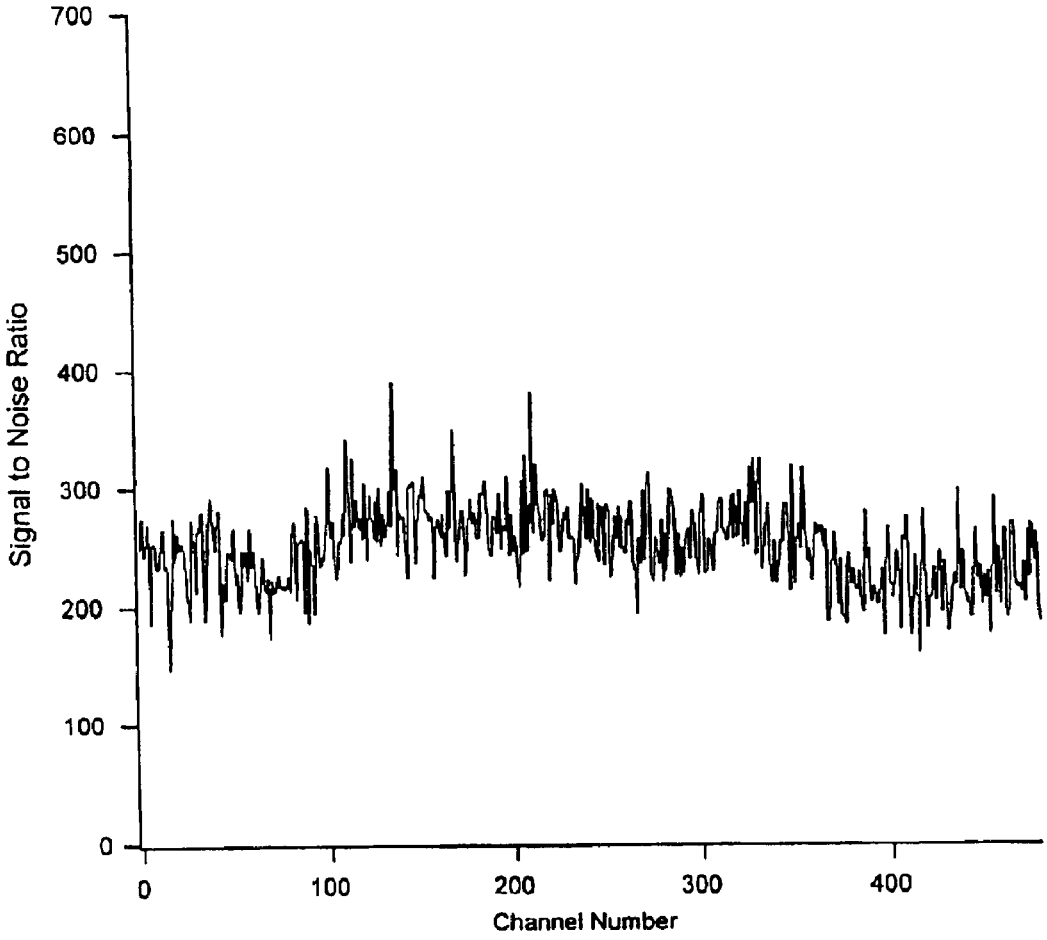
FIG. 5 is a plot of signal-to-noise ratio versus channel number for data collected across a 480-channel scan window without the velocity normalization.
Figure 6:
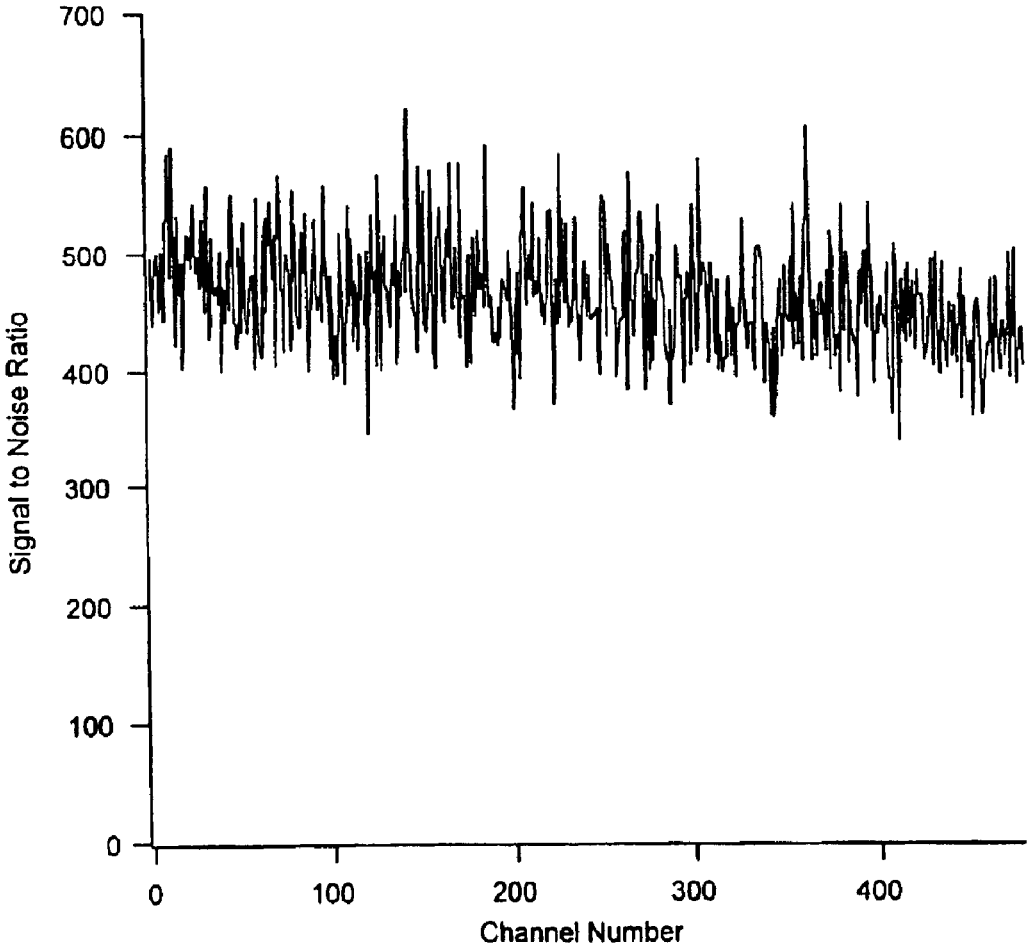
FIG. 6 is a plot similar to FIG. 5 but showing data collected employing velocity-normalization.

The noise that is most relevant to an actual sequencing experiment is the variation in signal intensity in a particular channel with respect to multiple scans. FIG. 5 is a plot of the signal to noise ratio versus channel number for data collected across a 480-channel scan window without velocity normalization (2.2.j firmware). The data plotted was from the red virtual filter only (i.e., the fourth virtual filter in the Plate Check A module). FIG. 6 is a similar plot of data collected with the velocity normalization method activated (2.2.n firmware). It is apparent from a comparison of FIGS. 5 and 6 that the signal to noise ratio of the data collected without velocity normalization is about one-half that of that of the data collected using velocity normalization.

Figure 7:
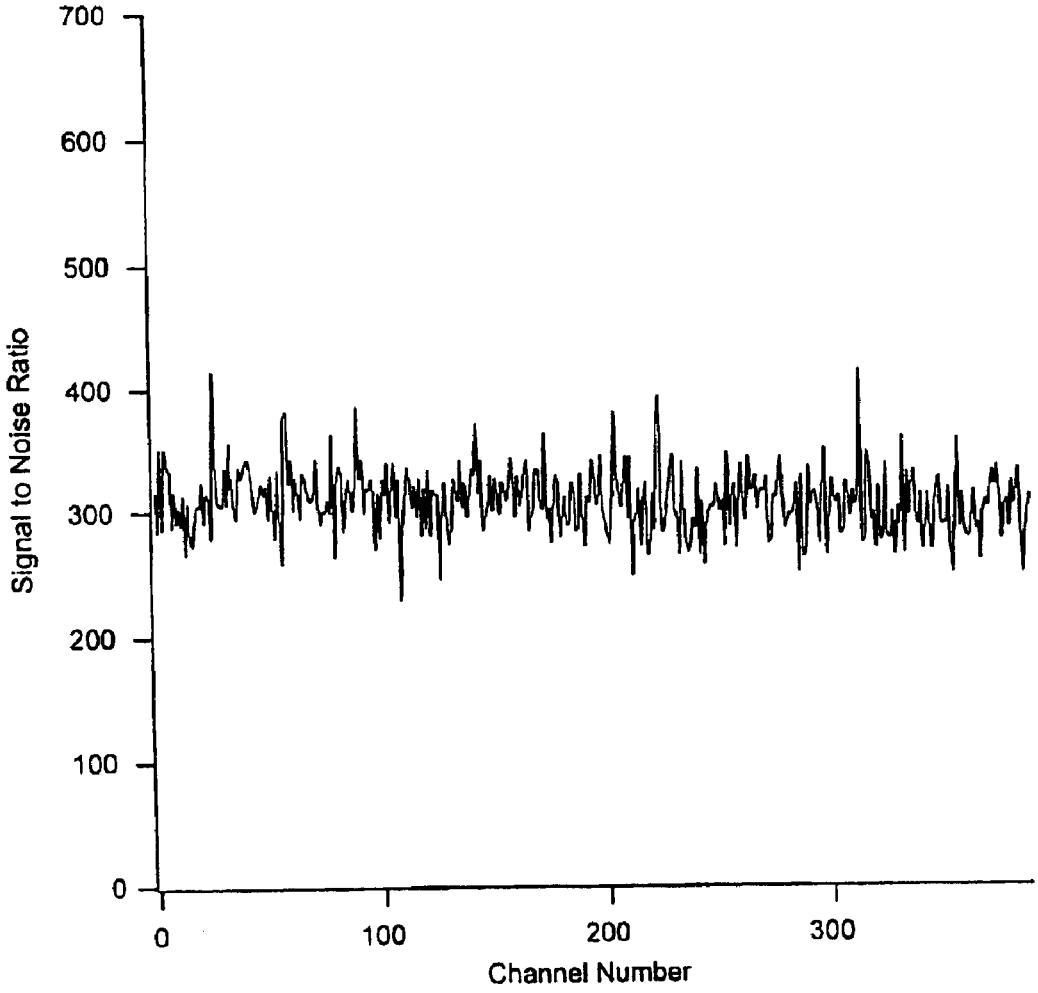
FIG. 7 is a plot of signal-to-noise ratio versus channel position across a 388-channel scan window using conventional time-based data collection.
Figure 8:
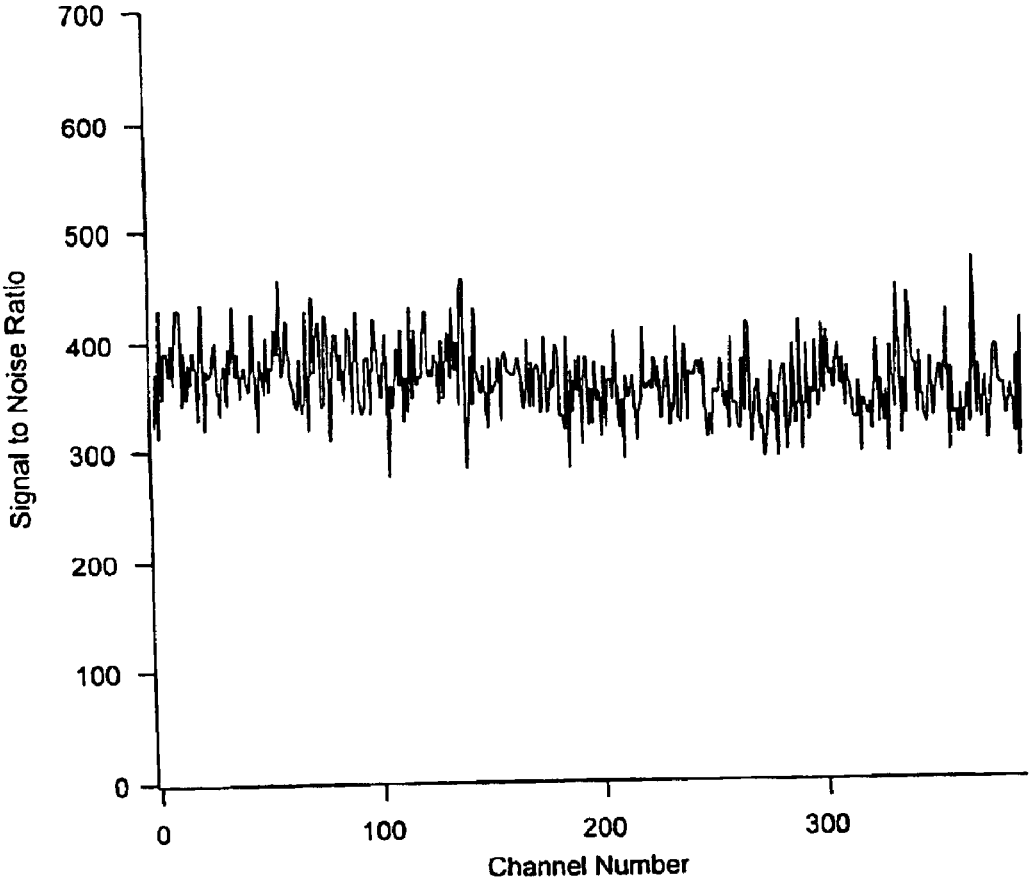
FIG. 8 is a plot similar to FIG. 7 but showing data collected employing velocity-normalization.

Comparison of data collected over a 388-channel scan window with velocity-normalized position based collection (2.2.n firmware) and conventional unnormalized time based collection (2.0 firmware) further demonstrates the efficacy of the velocity normalization method of the present invention. FIG. 7 is a plot of the signal-to-noise ratio versus channel position for a 388-channel scan window of data collected using conventional time-based data collection (2.0 firmware). As before, only data from the red virtual filter is shown. FIG. 8 is a plot of data from the same 388-channel scan window collected using the velocity-normalized position based collection method (2.2.n). From these plots it is evident that velocity-normalized position-based data collection is able to substantially reduce the noise due to changes in integration time inherent in conventional position-based data collection methods. In fact, the signal-to-noise ratio of the velocity-normalized position based collection is slightly larger than the signal-to-noise ratio of the time based collection. From a theoretical standpoint this is highly unexpected. The improved performance may be due to the fact that in time based acquisition scheme the integration time of each channel is determined by the instrument CPU. The CPU attempts to assign an equal integration time to each channel but the integration time can vary slightly depending on the processing load of the CPU. If the CPU is busy processing an interrupt service routine when a channel is read, data acquisition is delayed. In contrast, the position based collection scheme has integration times that vary considerably more than the time based firmware. However, the normalization method measures the actual integration time with the 16 Mhz clock at the moment of CCD readout. This measurement is extremely accurate and allows the firmware to achieve slightly lower noise than is possible even with time based data collection.

EXAMPLE 2

Sample Normalizing Procedure

The following are typical parameters obtained by performing a scan on an ABI PRISM™ 377 instrument. Units used are as follows. (1) Scanner motor encoder counts for distance. There are 1000 encoder counts per cm, or roughly 2500 per inch. (2) TIC (timer interrupt counts) for time. There are 4 million TICs per second. (3) A/D counts for CCD readouts. A fully saturated CCD would read 0×FFFF (65535) counts.

This experiment utilizes 194 data collection channels, over a distance of 6.2 inches (1.9 through 8.1 inches from the home position). Initially, the firmware calculates the start and end position of each channel—that is, the end position of one channel is the start position of the next. The following is a list of these encoder counts; the first value is the start of the first channel (#0), whereas the last value is the end count of the last channel (#193). Values are hexadecimal (base 16).

| | | | | | | | | | | | | |
|---|---|---|---|---|---|---|---|---|---|---|---|---|
| 128E | | | | | | | | | | | | |
| 12DD | 132D | 137D | 13CD | 141D | 146D | 14BD | 150D | 155D | 15AC | 15FC | 164C | 169C |
| 16EC | 173C | 178C | | | | | | | | | | |
| 17DC | 182C | 187C | 18CB | 191B | 196B | 19BB | 1A0B | 1A5B | 1AAB | 1AFB | 1B4B | 1B9B |

-continued

| | | | | | | | | | | | | |
|---|---|---|---|---|---|---|---|---|---|---|---|---|
| 1BEA | 1C3A | 1C8A | | | | | | | | | | |
| 1CDA | 1D2A | 1D7A | 1DCA | 1E1A | 1E6A | 1EB9 | 1F09 | 1F59 | 1FA9 | 1FF9 | 2049 | 2099 |
| 20E9 | 2139 | 2189 | | | | | | | | | | |
| 21D8 | 2228 | 2278 | 22C8 | 2318 | 2368 | 23B8 | 2408 | 2458 | 24AB | 24F7 | 2547 | 2597 |
| 25E7 | 2637 | 2687 | | | | | | | | | | |
| 26D7 | 2727 | 2777 | 27C6 | 2816 | 2866 | 28B6 | 2906 | 2956 | 29A6 | 29F6 | 2A46 | 2A96 |
| 2AE5 | 2B35 | 2B85 | | | | | | | | | | |
| 2BD5 | 2C25 | 2C75 | 2CC5 | 2D15 | 2D65 | 2DB5 | 2E04 | 2E54 | 2EA4 | 2EF4 | 2F44 | 2F94 |
| 2FE4 | 3034 | 3084 | | | | | | | | | | |
| 30D4 | 3123 | 3173 | 31C3 | 3213 | 3263 | 32B3 | 3303 | 3353 | 33A3 | 33F2 | 3442 | 3492 |
| 34E2 | 3532 | 3582 | | | | | | | | | | |
| 35D2 | 3622 | 3672 | 36C2 | 3711 | 3761 | 37B1 | 3801 | 3851 | 38A1 | 38F1 | 3941 | 3991 |
| 39E1 | 3A30 | 3A80 | | | | | | | | | | |
| 3AD0 | 3B20 | 3B70 | 3BC0 | 3C10 | 3C60 | 3CB0 | 3CFF | 3D4F | 3D9F | 3DEF | 3E3F | 3E8F |
| 3EDF | 3F2F | 3F7F | | | | | | | | | | |
| 3FCF | 401E | 406E | 40BE | 410E | 415E | 41AE | 41FE | 424E | 429E | 42EE | 433D | 438D |
| 43DD | 442D | 447D | | | | | | | | | | |
| 44CD | 451D | 456D | 45BD | 460C | 465C | 46AC | 46FC | 474C | 479C | 47EC | 4B3C | 4B8C |
| 48DC | 492B | 497B | | | | | | | | | | |
| 49CB | 4A1B | 4A6B | 4ABB | 4B0B | 4B5B | 4BAB | 4BFB | 4C4A | 4C9A | 4CEA | 4D3A | 4D8A |
| 4DDA | 4E2A | 4E7A | | | | | | | | | | |
| 4ECA | 4F1A | | | | | | | | | | | |

Next, an initial calibration scan is performed. For this purpose, every other channel spans across two positions in the list above, so that they become twice as wide. Four virtual filters are read from the CCD camera for each channel. In the end, the even and the odd channels are extracted and a median value is calculated for each virtual filter within each of these two different channel widths. These median values are then used for extrapolation to zero integration time. Separate scans are performed in the rightbound and leftbound directions. The following is a list of the median values at the narrow channel width (1t) and the twice-as-large channel width (2t), along with the extrapolated values that were used as a CCD offset, for normalization of values during the run. The median values are listed in hexadecimal (unsigned), whereas the extrapolated values are decimal, signed (They may go below zero due to a hardware offset in our instrument).

Rightbound baseline calibration

CCD Filter 0 baseline: <0B98/1t>, <13E0/2t> --> <848>
CCD Filter 1 baseline: <02A0/1t>, <0520/2t> --> <32>
CCD Filter 2 baseline: <0500/1t>, <09P0/2t> --> <16>
CCD Filter 3 baseline: <09C8/1t>, <1380/2t> --> <16>

Leftbound baseline calibration

CCD Filter 0 baseline: <0B9C/1t>, <13FE/2t> --> <826>
CCD Filter 1 baseline: <0294/1t>, <0531/2t> --> <-9>

-continued

CCD Filter 2 baseline: <04FC/1t>, <09D8/2t> --> <32>
CCD Filter 3 baseline: <09D3/1t>, <1370/2t> --> <54>

The collection scan was now started. Each channel was again defined by the same list of encoder counts calculated above, but this time none of the counts from that list were skipped. In other words, each value from that list represents the end point of one channel and the beginning of the next.

For each channel during the collection scan, a TIC (timestamp) is recorded, along with a signal indicating which virtual filter was being read from the CCD. At the end of each scan, normalization of the readings take place using these values. Also, a nominal integration time ($t_n$) was calculated:

<Nominal time=3415>

The following is a list of parameters used for scaling the first few channels. The information recorded is Channel number TIC (Timer Interrupt Count, or timestamp)

Calculated integration time (from one TIC to the next, i.e. start to end of the channel)

For each virtual filter reading, a normalized and scaled A/D count

<Ch = 0> <tic = FA2F>
<Ch = 1> <tic = 2CEC> <time = 32BD> <0: 0C42 -> 0C7E> <1: 0279 -> 0288> <2: 050D -> 052E> <3: 09B4 -> 09F5>
<Ch = 2> <tic = 60E4> <time = 33F8> <0: 0C3F -> 0C43> <1: 02B2 -> 02B3> <2: 0508 -> 050A> <3: 09FB -> 0A00>
<Ch = 3> <tic = 9567> <time = 3483> <0: 0C7B -> 0C67> <1: 029E -> 0298> <2: 0568 -> 055C> <3: 09FF -> 09EA>
<Ch = 4> <tic = C95D> <time = 33F6> <0: 0BEB -> 0BF0> <1: 02EB -> 02EC> <2: 0517 -> 0519> <3: 09BD -> 09C2>
<Ch = 5> <tic = FD6E> <time = 3411> <0: 0C11 -> 0C11> <1: 02A7 -> 02A7> <2: 050C -> 050C> <3: 09F0 -> 09F0>
<Ch = 6> <tic = 316A> <time = 33FC> <0: 0C07 -> 0C0B> <1: 0279 -> 027A> <2: 052E -> 0530> <3: 0A0D -> 0A11>
<Ch = 7> <tic = 65B6> <time = 344C> <0: 0C36 -> 0C2C> <1: 027F -> 027C> <2:

-continued

051F –> 0519> <3: 09BF –> 09B4>
<Ch = 8> <tic = 99BF> <time = 3409> <0: 0C3E –> 0C40> <1: 02AC –> 02AC> <2: 04EC –> 04ED> <3: 098F –> 0991>
<Ch = 9> <tic = CDDA> <time = 341B> <0: 0BEA –> 0BE9> <1: 0277 –> 0276> <2: 0507 –> 0506> <3: 09CF –> 09CD>
<Ch = 10> <tic = 015C> <time = 3382> <0: 0BF5 –> 0C0D> <1: 0283 –> 0289> <2: 051F –> 052D> <3: 09B8 –> 09D3>
<Ch = 11> <tic = 3535> <time = 33D9> <0: 0BCF –> 0BD6> <1: 0267 –> 0269> <2: 0507 –> 050C> <3: 09F2 –> 09FD>
<Ch = 12> <tic = 691E> <time = 33E9> <0: 0BDD –> 0BE4> <1: 029F –> 02A1> <2: 052B –> 052F> <3: 09CD –> 09D5>
<Ch = 13> <tic = 9D91> <time = 3473> <0: 0C3D –> 0C2D> <1: 02AE –> 02A9> <2: 050F –> 0506> <3: 0A0A –> 09F8>
<Ch = 14> <tic = D16C> <time = 33DB> <0: 0BBF –> 0BC8> <1: 0277 –> 0279> <2: 053C –> 0541> <3: 09DC –> 09E6>
<Ch = 15> <tic = 05B5> <time = 3449> <0: 0BC9 –> 0BC0> <1: 0283 –> 0280> <2: 0519 –> 0513> <3: 09DA –> 09D0>
<Ch = 16> <tic = 39CD> <time = 3418> <0: 0C13 –> 0C12> <1: 027D –> 027C> <2: 0542 –> 0541> <3: 09CE –> 09CD>
<Ch = 17> <tic = 6DD9> <time = 340C> <0: 0C17 –> 0C18> <1: 02A4 –> 02A4> <2: 04F8 –> 04F8> <3: 0A23 –> 0A24>
<Ch = 18> <tic = A1DA> <time = 3401> <0: 0BDD –> 0BE0> <1: 0274 –> 0274> <2: 0505 –> 0506> <3: 09DF –> 09E2>
<Ch = 19> <tic = D640> <time = 3466> <0: 0BAF –> 0BA2> <1: 02BE –> 02B9> <2: 04CF –> 04C7> <3: 09CF –> 09BF>
<Ch = 20> <tic = 0955> <time = 3315> <0: 0BE6 –> 0C11> <1: 0253 –> 025E> <2: 050C –> 0524> <3: 09A7 –> 09D7>
<Ch = 21> <tic = 3D9A> <time = 3445> <0: 0B87 –> 0B7F> <1: 029A –> 0297> <2: 053E –> 0539> <3: 09B6 –> 09AD>
<Ch = 22> <tic = 7149> <time = 33AF> <0: 0BC7 –> 0BD7> <1: 0287 –> 028B> <2: 04DF –> 04E8> <3: 09C8 –> 09DB>
<Ch = 23> <tic = A5A2> <time = 3459> <0: 0BF7 –> 0DEB> <1: 02AF –> 02AB> <2: 0515 –> 050E> <3: 0A2B –> 0A1D>
<Ch = 24> <tic = D9C2> <time = 3420> <0: 0BE7 –> 0BE5> <1: 027F –> 027E> <2: 0519 –> 0517> <3: 09CF –> 09CC>
<Ch = 25> <tic = 0DBC> <time = 33FA> <0: 0C0E –> 0C12> <1: 02AA –> 02AB> <2: 0503 –> 0505> <3: 0A12 –> 0A17>

All publications and patent applications are herein incorporated by reference to the same extent as if each individual publication or patent application was specifically and individually indicated to be incorporated by reference.

Although only a few embodiments have been described in detail above, those having ordinary skill in the scanning art will clearly understand that many modifications are possible in the preferred embodiment without departing from the teachings thereof. All such modifications are intended to be encompassed within the following claims.

I claim:

1. A data collection method for scanning a scan window comprising one or more channels comprising the steps of:

detecting an integrated signal (S) across [a] *the* scan window comprising one or more channels using an integrating detector; and calculating a velocity-normalized integrated signal (Sn) as a function of a scan velocity and the integrated signal S.

2. The method of claim 1 wherein the step of calculating the velocity-normalized integrated signal (Sn) comprises:

determining a scan velocity, v; and dividing the integrated signal S by the scan velocity v.

3. The method of claim 1 wherein the step of calculating the velocity-normalized integrated signal (Sn) comprises:

measuring a channel width (w);

determining a time for traversing the channel width (t); and computing [a] *the* velocity-normalized integrated signal according to the equation Sn=S/(w/t).

4. The method of claim 1 wherein the step of calculating the velocity-normalized integrated signal (Sn) comprises subtracting a detector offset So from [an] *the* integrated signal (S).

5. The method of claim 1 wherein the channels are disposed in a linear array.

6. The method of claim 1 wherein the channels are lanes in a multilane electrophoresis system.

7. The method of claim 6 wherein the lanes are located in a slab gel.

8. The method of claim 6 wherein the lanes are located in isolated electrophoresis channels.

9. The method of claim 6 wherein [the lane density of] the multilane electrophoresis system [is] *has a lane density of* at least 1.8 mm/lane.

10. The method of claim 1 wherein the step of detecting an integrated signal across a scan window is effected using a stepper motor to cause a relative motion between the scan window and the integrating detector.

11. The method of claim 10 wherein a channel width (w) is measured by counting steps in the stepper motor.

12. The method of claim 11 wherein a position sensor is used to define a home position for initializing the stepper motor.

13. The method of claim 1 wherein the integrating detector is a CCD or a photodiode array.

14. The method of claim 1 wherein the integrated signal results from detection of a fluorescence emission.

15. The method of claim 14 wherein the fluorescence emission is stimulated by a laser.

16. An apparatus for scanning a plurality of channels comprising:

means for detecting an integrated signal (S) across a scan window comprising [one or more] *the plurality of* channels using an integrating detector; and computer means for receiving the integrated signal S and determining a scan velocity and for calculating a velocity-normalized integrated signal (Sn) as a function of the scan velocity and the integrated signal S.

17. An apparatus for scanning a scan window having one or more channels comprising:

an integrating detector;

a scanner for effecting a scanning of the integrating detector relative to [a] *the* scan window comprising one or more channels, *wherein an integrated signal (S) is detected by scanning the integrating detector relative to the scan window*; and a computer for receiving the integrated signal S and for determining a scan velocity and for calculating a velocity-normalized integrated signal (Sn).

18. The apparatus of claim 17 wherein the integrating detector is a charged coupled device.

19. The apparatus of claim 17 wherein the scanner comprises a stepper motor.

20. The apparatus of claim 17 wherein the scan window comprises multiple electrophoresis lanes.

21. A program storage device readable by a machine, tangibly embodying a program of instructions executable by a machine to perform method steps to scan a scan window comprising one or more channels, said method steps comprising:

detecting an integrated signal (S) across a scan window comprising one or more channels using an integrating detector; and calculating a velocity-normalized integrated signal (Sn) as a function of a scan velocity and the integrated signal S.

22. The program storage device of claim 21 wherein the step of calculating the velocity-normalized integrated signal (Sn) comprises:

determining a scan velocity, v; and dividing the integrated signal S by the scan velocity v.

23. The program storage device of claim 21 wherein the step of calculating the velocity-normalized integrated signal (Sn) comprises:

measuring a channel width (w);

determining a time for traversing the channel width (t); and computing [a] *the* velocity-normalized integrated signal according to the equation Sn=S/(w/t).

24. The program storage device of claim 21 wherein the step of calculating the velocity-normalized integrated signal (Sn) comprises subtracting a detector offset So from an integrated signal (S).

25. The program storage device of claim 24 wherein [a] *the* channel width (w) is measured by counting steps in the stepper motor.

*26. The method of claim 1, further comprising determining an integration time (ti) for the integrated signal; and*

*wherein the calculating the velocity-normalized integrated signal comprises dividing the integrated signal (S) by the integration time (ti),*

*and wherein the scan window comprises more than one channel.*

*27. The method of claim 26, wherein determining the integration time (ti) comprises determining a start time (ts) at a start of the detecting the integrated signal; determining an end time (te) at an end of the detecting the integrated signal; and determining the integration time (ti) as a difference of the end time (te) and the start time (ts).*

*28. The method of claim 27, wherein the integrating detector comprises at least one of a CCD and a photodiode array.*

*29. The apparatus of claim 16, furthering comprising means for determining an integration time (ti) for the integrated signal; and wherein the calculating the velocity-normalized integrated signal comprises dividing the integrated signal (S) by the integration time (ti).*

*30. The apparatus of claim 29, wherein determining the integration time (ti) comprises determining a start time (ts) at a start of the detecting the integrated signal; determining an end time (te) at an end of the detecting the integrated signal; and determining the integration time (ti) as a difference of the end time (te) and the start time (ts).*

*31. The apparatus of claim 30, further comprising the integrating detector.*

*32. The apparatus of claim 17, further comprising a timer configured to determine an integration time (ti) for the integrated signal; and wherein the calculating the velocity-normalized integrated signal comprises dividing the integrated signal (S) by the integration time (ti), and the scan window comprises more than one channel.*

*33. The apparatus of claim 32, wherein determining the integration time (ti) comprises determining a start time (ts) at a start of the detecting the integrated signal; determining an end time (te) at an end of the detecting the integrated signal; and determining the integration time (ti) as a difference of the end time (te) and the start time (ts).*

*34. The program storage device of claim 21, wherein the method further comprises determining an integration time (ti) for the integrated signal (S); the calculating the velocity-normalized integrated signal (Sn) comprises dividing the integrated signal (S) by the integration time (ti); and the scan window comprises more than one channel.*

*35. The program storage device of claim 34, wherein determining the integration time (ti) comprises determining a start time (ts) at a start of the detecting the integrated signal; determining an end time (te) at an end of the detecting the integrated signal; and determining the integration time (ti) as a difference of the end time (te) and the start time (ts).*

*36. An apparatus for scanning one or more channels comprising:*

*means for detecting an integrated signal (S) across a scan window comprising one or more channels using an integrating detector; and*

*computer means for receiving the integrated signal S and determining a scan velocity and for calculating a velocity-normalized integrated signal (Sn) as a function of the scan velocity and the integrated signal S.*

*37. The apparatus according to claim 36, further comprising the integrating detector.*

*38. A data collection method for scanning a scan window comprising:*

*detecting an integrated signal (S) across the scan window comprising one or more channels using an integrating detector;*

*determining an integration time (ti) for the integrated signal; and*

*calculating a velocity-normalized integrated signal (Sn), the calculating comprising dividing the integrated signal (S) by the integration time (ti).*

*39. The method of claim 38, wherein determining the integration time (ti) comprises determining a start time (ts) at a start of the detecting the integrated signal; determining an end time (te) at an end of the detecting the integrated signal; and determining the integration time (ti) as a difference of the end time (te) and the start time (ts).*

*40. The method of claim 39, further comprising determining a detector offset (So); determining an offset adjusted unnormalized signal as the difference (S–So); and wherein the calculating the velocity-normalized integrated signal (Sn) comprises dividing the offset adjusted unnormalized signal by the integration time (ti).*

*41. The method of claim 40, wherein determining the offset adjusted unnormalized signal further comprises multiplying the difference (S–So) by a scaling factor (tn).*

*42. The method of claim 39, wherein the channels are disposed in a linear array.*

*43. The method of claim 39, wherein the channels comprise lanes in a multilane electrophoresis system.*

*44. The method of claim 43, wherein the lanes are located in a slab gel.*

*45. The method of claim 43, wherein the lanes are located in isolated electrophoresis channels.*

*46. The method of claim 43, wherein the multilane electrophoresis system has a lane density of at least 1.8 mm/lane.*

*47. The method of claim 39, wherein detecting the integrated signal comprises using a stepper motor to cause a relative motion between the scan window and the integrating detector.*

*48. The method of claim 47, wherein a position sensor is used to define a home position for initializing the stepper motor.*

*49. The method of claim 39, wherein the integrating detector comprises at least one of a CCD and a photodiode array.*

*50. The method of claim 39, wherein the integrated signal results from detection of a fluorescence emission.*

*51. The method of claim 50, wherein the fluorescence emission is stimulated by a laser.*

*52. An apparatus for scanning one or more channels comprising:*

*means for detecting an integrated signal (S) across a scan window comprising one or more channels using an integrating detector;*

*means for determining an integration time (ti) for the integrated signal; and*

*computer means for receiving the integrated signal (S) and the integration time (ti), and for determining a velocity-normalized integrated signal (Sn), the determining comprising dividing the integrated signal (S) by the integration time (ti).*

*53. The apparatus of claim 52, wherein determining the integration time (ti) comprises determining a start time (ts) at a start of the detecting the integrated signal; determining an end time (te) at an end of the detecting the integrated signal; and determining the integration time (ti) as a difference of the end time (te) and the start time (ts).*

*54. The apparatus of claim 53, wherein the computer means comprises the means for determining the integration time (ti).*

*55. The apparatus of claim 53, further comprising the integrating detector.*

*56. An apparatus for scanning a scan window having one or more channels comprising:*

*an integrating detector;*

*a scanner configured to scan the integrating detector relative to the scan window, wherein an integrated signal (S) is detected by scanning the integrating detector relative to the scan window;*

*a timer configured to determine an integration time (ti) for the integrated signal; and*

*a computer configured to receive the integrated signal (S) and the integration time (ti), and to determine a velocity-normalized integrated signal (Sn), the determining comprising dividing the integrated signal (S) by the integration time (ti).*

*57. The apparatus of claim 56, wherein determining the integration time (ti) comprises determining a start time (ts) at a start of the detecting the integrated signal; determining an end time (te) at an end of the detecting the integrated signal; and determining the integration time (ti) as a difference of the end time (te) and the start time (ts).*

*58. The apparatus of claim 57, wherein the computer is configured to determine the integration time (ti).*

*59. The apparatus of claim 57, wherein the integrating detector comprises a charged coupled device.*

*60. The apparatus of claim 57, wherein the scanner comprises a stepper motor.*

*61. The apparatus of claim 57, wherein the scan window comprises multiple electrophoresis lanes.*

*62. A program storage device readable by a machine, tangibly embodying a program of instructions executable by a machine to perform a method to scan a scan window comprising one or more channels, said method comprising:*

*detecting an integrated signal (S) across a scan window comprising one or more channels using an integrating detector;*

*determining an integration time (ti) for the integrated signal (S); and*

*calculating a velocity-normalized integrated signal (Sn), the calculating comprising dividing the integrated signal (S) by the integration time (ti).*

*63. The program storage device of claim 62, wherein determining the integration time (ti) comprises determining a start time (ts) at a start of the detecting the integrated signal; determining an end time (te) at an end of the detecting the integrated signal; and determining the integration time (ti) as a difference of the end time (te) and the start time (ts).*

*64. The program storage device of claim 63, wherein the method further comprises determining a detector offset (So); determining an offset adjusted unnormalized signal as the difference (S–So); and wherein the calculating the velocity-normalized integrated signal (Sn) comprises dividing the offset adjusted unnormalized signal by the integration time (ti).*

*65. The program storage device of claim 64, wherein determining the offset adjusted unnormalized signal further comprises multiplying the difference (S–So) by a scaling factor (tn).*

* * * * *

UNITED STATES PATENT AND TRADEMARK OFFICE

CERTIFICATE OF CORRECTION

PATENT NO. : RE 38,817 E
DATED : October 11, 2005
INVENTOR(S) : Tor Slettnes

It is certified that error appears in the above-identified patent and that said Letters Patent is hereby corrected as shown below:

Column 13,
Line 66, "furthering" should read -- further --.

Signed and Sealed this

Thirtieth Day of May, 2006

JON W. DUDAS
*Director of the United States Patent and Trademark Office*